United States Patent
Frank et al.

(10) Patent No.: US 11,357,694 B2
(45) Date of Patent: Jun. 14, 2022

(54) FOOT WRAP WITH INFLATABLE BLADDER

(71) Applicant: ALBAHEALTH, LLC, Rockwood, TN (US)

(72) Inventors: Mary H Frank, Cookeville, TN (US); William M. Davidson, Knoxville, TN (US); Shane C. Bruce, Lenoir City, TN (US)

( * ) Notice: Subject to any disclaimer, the term of this patent is extended or adjusted under 35 U.S.C. 154(b) by 1084 days.

(21) Appl. No.: 15/585,995

(22) Filed: May 3, 2017

(65) Prior Publication Data

US 2017/0333281 A1 Nov. 23, 2017

Related U.S. Application Data

(63) Continuation-in-part of application No. 12/191,719, filed on Aug. 14, 2008, now abandoned.

(51) Int. Cl.
*A61H 9/00* (2006.01)

(52) U.S. Cl.
CPC ......... *A61H 9/0078* (2013.01); *A61H 9/0071* (2013.01); *A61H 2201/0103* (2013.01); *A61H 2201/1238* (2013.01); *A61H 2201/165* (2013.01); *A61H 2201/169* (2013.01); *A61H 2201/1642* (2013.01); *A61H 2201/1645* (2013.01); *A61H 2201/5056* (2013.01); *A61H 2205/12* (2013.01)

(58) Field of Classification Search
CPC .............. A61H 2205/12; A61H 9/0078; A61H 2209/00; A61H 23/04; A61H 9/0071; A61H 9/00; A61H 9/005; A61H 2201/0103; A61H 2201/1238; A61H 2201/1642; A61H 2201/1645; A61H 2201/165; A61H 2201/169; A61H 2201/5056; A61F 2007/0045; A61F 2007/0094; A61F 2007/0091; A61F 5/14; A61F 5/30; A61F 5/012; A61F 5/05816; A61F 5/0102; A61F 5/0585; A61F 5/0111; A61F 5/0127; A61F 5/0113; A61F 5/34; Y10S 128/20; A61B 2090/401; A43B 13/20
USPC ....... 601/148, 151, 152, 153, 104, 149, 150, 601/22; 602/13, 23, 1, 5, 27, 28, 29; 36/141, 150, 153; 606/201–203; 2/DIG. 3; 128/DIG. 20, 118.1, 847, 869, 128/882
See application file for complete search history.

(56) References Cited

U.S. PATENT DOCUMENTS

| | | | |
|---|---|---|---|
| 5,643,315 A * | 7/1997 | Daneshvar | A61B 17/135 606/201 |
| 6,319,215 B1 * | 11/2001 | Manor | A61H 9/0078 601/148 |
| 2006/0178606 A1 * | 8/2006 | Logue | A61F 5/012 602/23 |

(Continued)

*Primary Examiner* — Caitlin A Carreiro
(74) *Attorney, Agent, or Firm* — Baker Donelson

(57) ABSTRACT

A foot wrap (10) has a generally non-stretchable, flexible binding (11), a generally stretchable panel (12) coupled to the binding, an expandable, rotatable bladder (14), and a support pad (16) coupled to the binding opposite the bladder (14). The binding has a central portion (19) straddled by a first wing (21), a second wing (22), and an elastic heel band (23). The bladder measures approximately 3 inches by 3 inches and is designed to increase in height approximately 1½ to 1¾ inches with its inflation.

8 Claims, 3 Drawing Sheets

(56) References Cited

U.S. PATENT DOCUMENTS

2007/0135743 A1\* 6/2007 Meyer .................... A61F 13/06
601/152
2007/0288095 A1\* 12/2007 Wirtel .................... A61F 2/442
623/17.16

\* cited by examiner

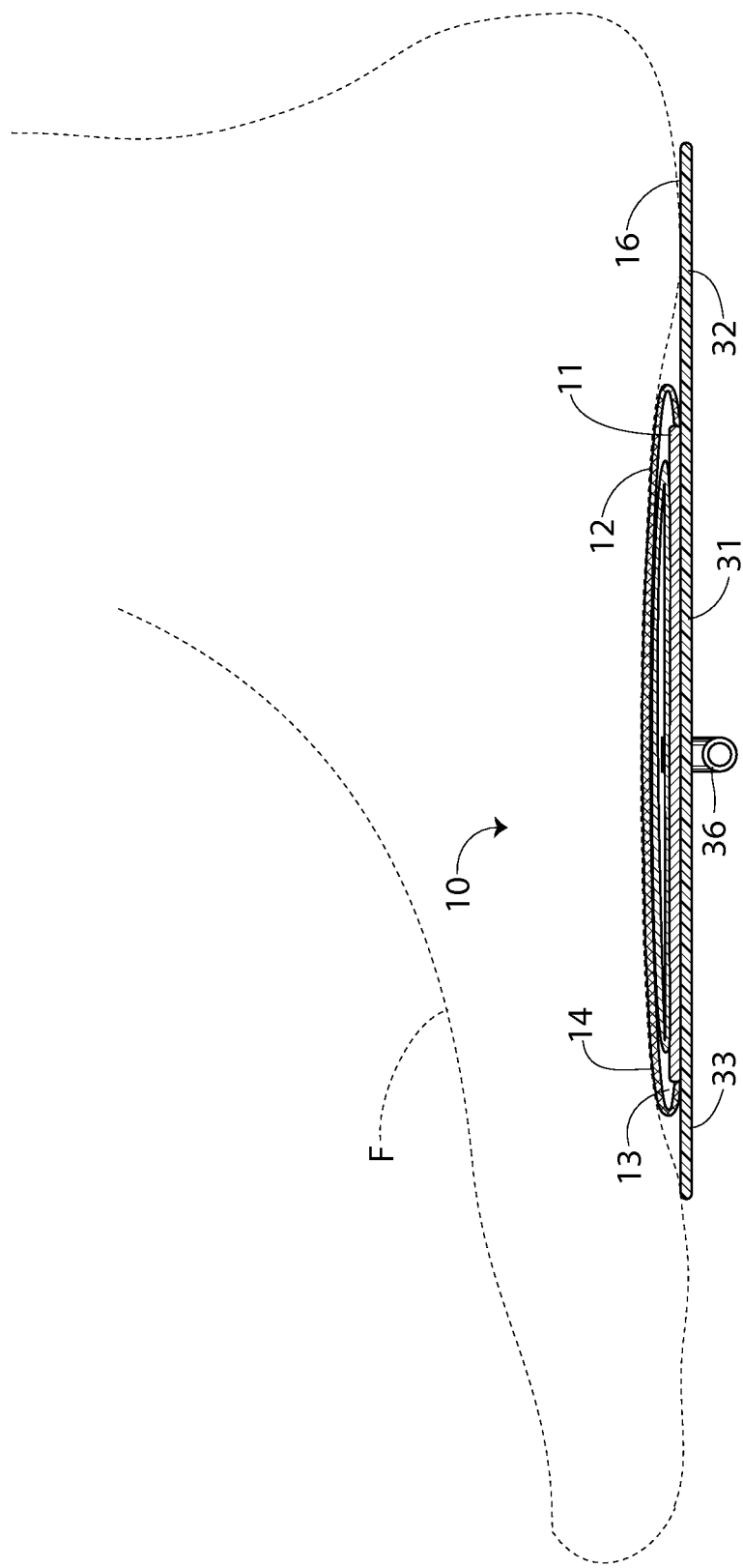

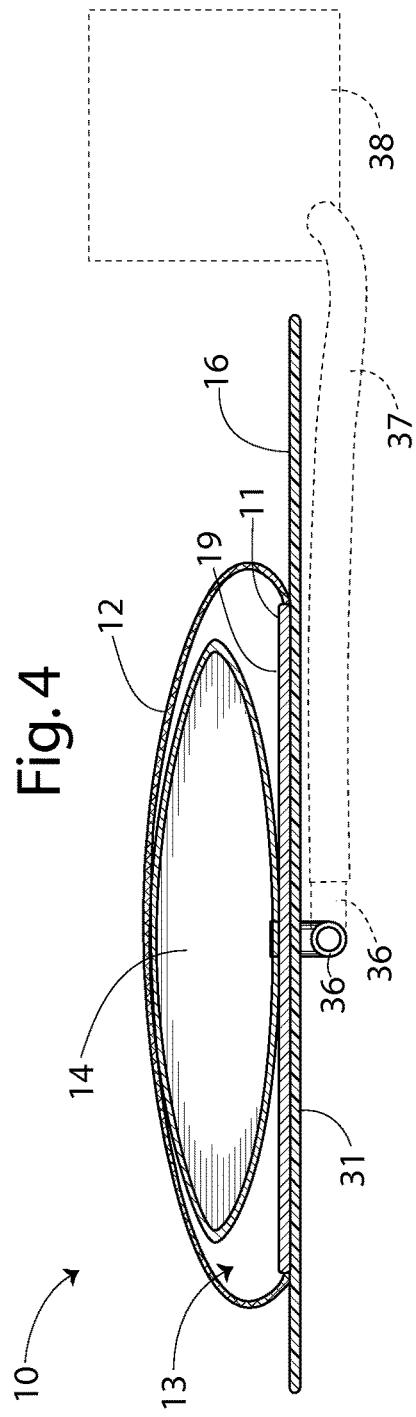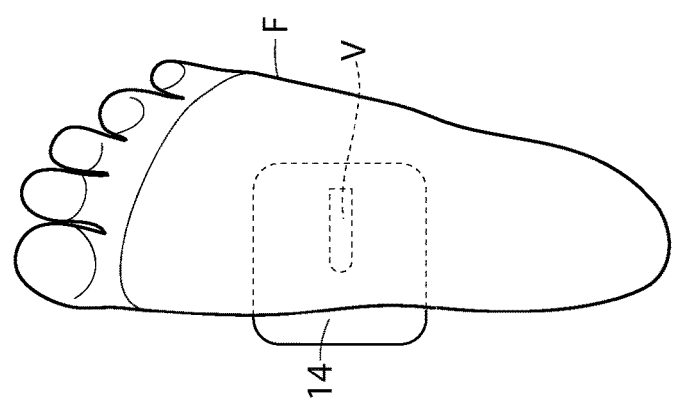

FOOT WRAP WITH INFLATABLE BLADDER

REFERENCE TO RELATED APPLICATION

This is a continuation-in-part of U.S. patent application Ser. No. 12/191,719 filed Aug. 14, 2008.

TECHNICAL FIELD

This invention relates to foot wraps for pneumatically applying pressure to the foot to improve circulation in a limb extremity.

BACKGROUND OF THE INVENTION

Walking or running is known to increase circulation in the leg because doing so puts pressure on the venous plexus vein located on the arch portion of a foot. Foot wraps have been used to increase blood circulation by simulating walking or running upon the venous plexus vein. This is accomplished by cyclically inflating a bladder housed within a foot wrap so that the bladder applies pressure upon the venous plexus vein. In order for a foot wrap to be beneficial to the user, it must be properly placed underneath the arch and air from a pneumatic pump coupled to the foot wrap must continually travel through a conduit to cyclically inflate and deflate the bladder within the foot wrap. A problem associated with prior art foot wraps is that their construction does not provide maximum compression of the venous plexus vein with each inflation of the bladder.

Accordingly, it is seen that a need remains for a foot wrap that provides maximum pressure to the venous plexus vein with each inflation of the bladder. It is to the provision of such therefore that the present invention is primarily directed.

SUMMARY OF THE INVENTION

In a preferred form of the invention a foot wrap comprises a support pad, a non-stretchable binding coupled to the support pad, the non-stretchable binding having at least a central portion overlaying the support pad, and a stretchable panel overlying the non-stretchable binding central portion. The stretchable panel and the non-stretchable binding central portion define a bladder chamber. The foot wrap also includes an expandable bladder positioned within the bladder chamber for rotational movement of the expandable bladder relative to the bladder chamber of at least 30 degrees. With this construction, the expansion of the bladder is restricted from expanding in one direction by the non-stretchable binding central portion but allowed to readily expand in an opposite direction by the stretchable panel.

BRIEF DESCRIPTION OF THE DRAWING

FIG. 3 is a cross-sectional view of the foot wrap of FIG. 1, shown with a bladder in a deflated condition.

FIG. 4 is a cross-sectional view of the foot wrap of FIG. 1, shown with a bladder in an inflated condition.

FIG. 5 is a bottom view of a foot showing the placement of a bladder of the foot wrap of FIG. 1.

DETAILED DESCRIPTION

Figure 1:
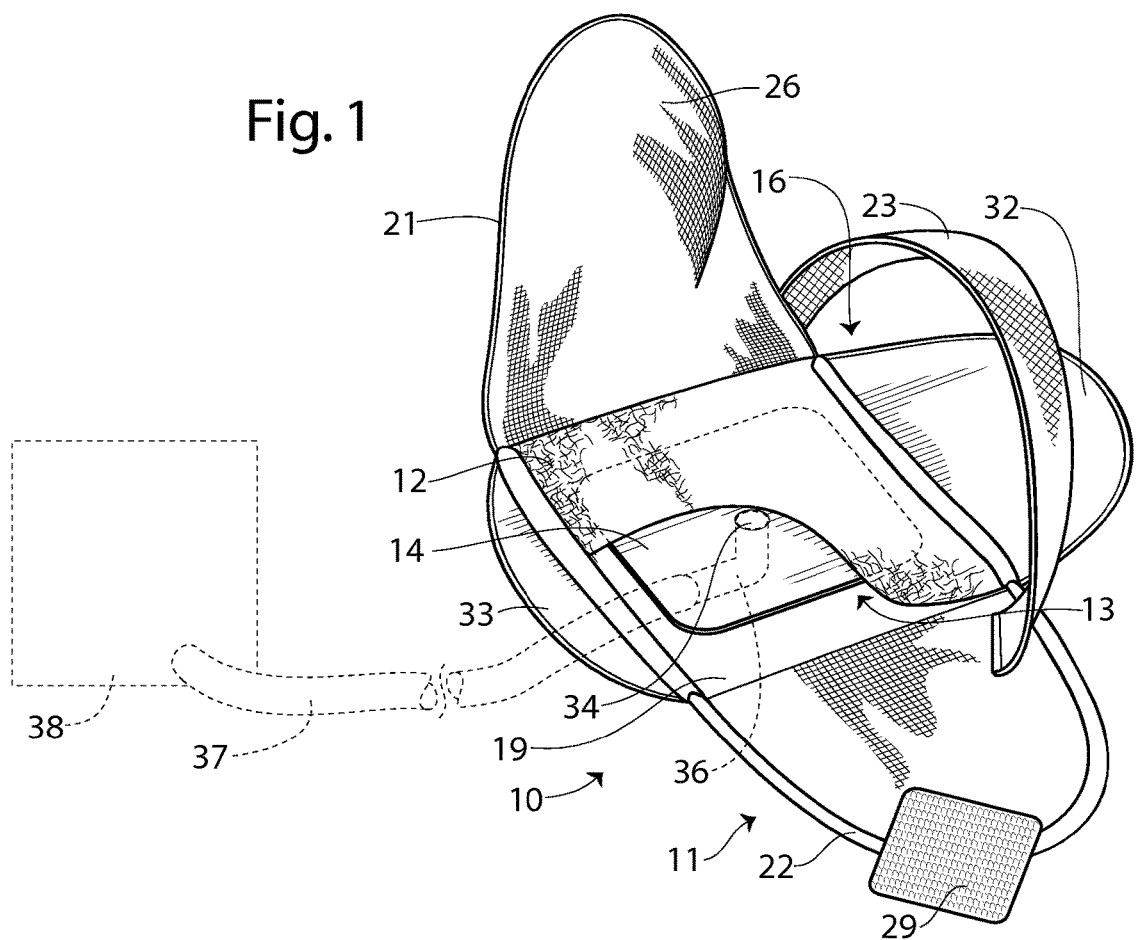
FIG. 1 is a perspective view of a foot wrap, shown with a portion removed, embodying principles of the invention in a preferred form.

With reference next to the drawings, there is shown a foot wrap 10 in a preferred form of the invention. The foot wrap 10 includes a generally non-stretchable binding or wrap portion 11, a generally stretchable panel 12 coupled to the binding 11 along at least a portion of its peripheral margin so as to define a bladder chamber 13 therebetween, an expandable bladder 14 positioned within the bladder chamber 13, and a support pad 16 coupled to the binding 11 opposite the bladder 14.

The binding 11 has a central portion 19 straddled by a first wing 21, a second wing 22 opposite the first wing 21, and an elastic heel band 23 fixed to the first wing 21 and removably coupled to the second wing 22 through a hook type fastener 24 mounted to the end of the band. The first wing 21 has an inner layer 26 comprised of a generally non-stretchable woven material. It should be understood that most materials have some quantity of stretch associated with the material, as such as used herein the term generally non-stretchable woven material is intended to reflect a flexible material which has a minimal amount of stretch such as a plain weave material which utilizes spun yarns with a poly/cotton blend and a weight characteristic of 4 to 7 ounces per square yard. The first wing 21 also has an outer layer 27 comprised of a unbroken loop (UBL) material, such as a brushed nylon, as for example that manufactured by Gehring Textiles, Inc. of New York, N.Y. under model number 1788 or by Rentex Mills, Inc. of Mont-Royal, Quebec, Canada under model number R6026. The outer layer 27 is suitable as the loop portion of hook and loop type fasteners. The central portion 19 and second wing 22 are made of the same non-stretchable woven material as the inner layer 26 of the first wing, and as such, may be made of unitary construction therewith. The second wing 22 also includes a tab 29 of hook type fasteners which are capable of releasably fastening to the outer layer 27 of first wing 21.

The generally stretchable panel 12 is also comprised of an unbroken loop (UBL) material which may be the same as that previously described. The panel 12 material is stretchable to allow the unencumbered inflation of the bladder 14, i.e., it stretches upon inflation of the bladder so as not to substantially restrict such from occurring.

The support pad 16 has a central panel 31, a heel panel 32 and a forward panel 33. The heel panel and forward panel are pivotal relative to the central panel. The central panel 32 has a central hole 34 therethrough. The support pad 16 may be made of polyethylene (PET) foam material.

The bladder 14 may be made of an 11 mil vinyl material. The bladder 14 measures approximately 3 inches by 3 inches and is generally square in shape. Of course, it should be understood that the bladder may be of different dimensions and of different shapes. With this configuration, the bladder's height, as shown in FIGS. 3 and 4 of the drawings, increases to approximately 1¼ to 1¾ inches with its inflation. The bladder 14 has a centrally positioned L-shaped intake coupler 36, which extends through hole 34 within the support pad central panel 31. The intake coupler 36 is coupled to a pneumatic pressure line or hose 37 coupled at its opposite end to an intermittent compression pneumatic pump 38 which cyclically inflates and deflates the bladder, such as an intermittent compression pump made by Albahealth, LLC of Rockwood, Tenn., under the trade name PAS II Pulsatile.

Figure 2:
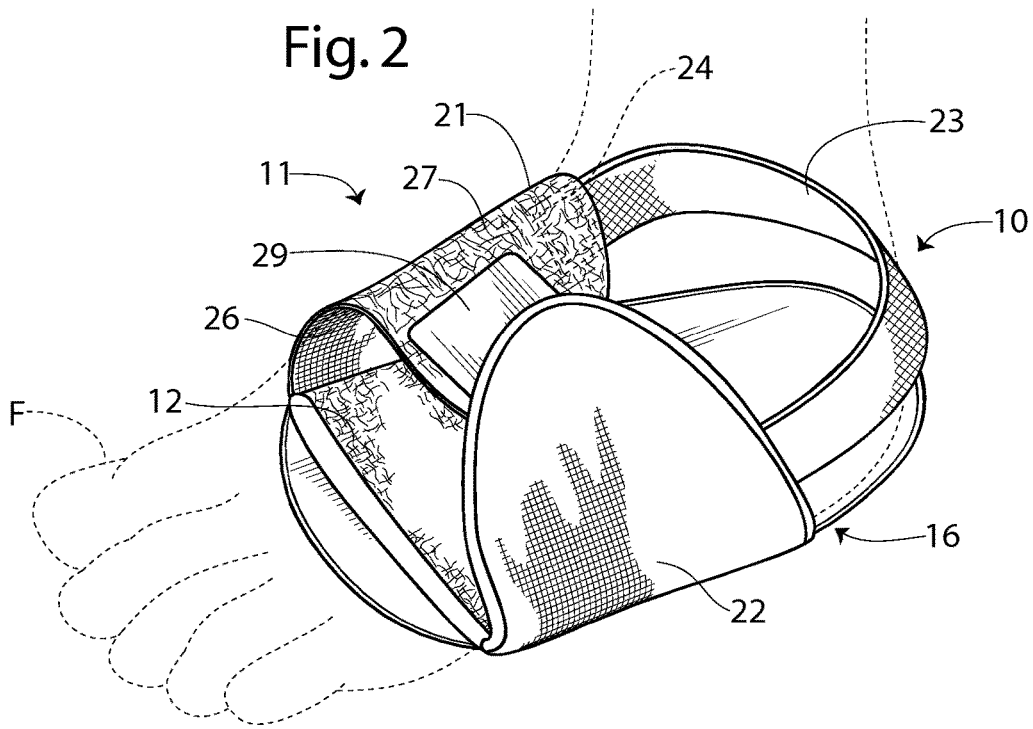
FIG. 2 is a perspective view of the foot wrap of FIG. 1 shown mounted to a foot.

In use, the foot wrap 10 is mounted to a person's foot F by positioning the foot upon the support pad 16, wrapping the first wing 21 about the top of the foot, wrapping the second wing 22 about the top of the foot and first wing and engaging the hook fasteners of tab 29 to the outer layer 27 of the first wing. The heel band 23 is then stretched and wrapped about the heel of the foot and coupled to the outer layer 27 of the first wing 21 through the hook type fastener 24. The bladder 14 should be positioned directly below the venous plexus vein V. The mounted foot wrap 10 is best shown in FIGS. 2 and 5.

With the bladder 14 coupled to the intermittent compression pneumatic pump 38 through the hose 37 and intake coupler 36, the passage of pressurized air into the bladder 14 causes the bladder to inflate and thereby expand. The expansion of the bladder 14 is restricted in the direction opposite to the foot by the non-stretchable characteristic of the wrap binding 11, but unrestricted in the opposite direction, towards the foot, by the stretchable characteristic of the stretchable panel 12. As such, the expanding movement of the bladder 14 is deflected or concentrated towards the wearer's foot and onto the venous plexus vein. This concentrated movement of the bladder is a departure from the prior art devices which generally allow unrestricted movement of the bladder in all directions, thereby causing some forces associated with the inflation of the bladder to be lost as the bladder expands away from the foot. The present invention with its higher concentration of the bladder movement towards the foot allows the bladder to work more efficiently, i.e., requiring less air pressure and/or less bladder expansion per inflation cycle.

An additional benefit of the present invention is the unrestricted, complete rotatability of the bladder 14 within the bladder chamber 13. The rotation of the bladder 14 allows the intake coupler 36, and adjoining pneumatic hose 37, to be fully rotated or repositioned for a complete 360 degree rotation about a vertical axis within the bladder chamber 13 to any position relative to the foot. This allows the hose 37 to be directed to the nearest egress to reduce the likelihood of kinking or pinching the hose or interference of the hose against the wearer of the foot wrap. While a 360 degree horizontal rotation about a vertical axis is optimal, the rotation may be limited to at least 90 degrees, and perhaps as little as 30 degrees even though such a limited amount of rotation is not truly desired. Of course, it should be understood that as an alternative, the coupler 36 may also be made rotatable relative to the expanding portion of the bladder. The rotation of the coupler may be as little as 30 degrees, however, it is believed that a fully rotatable coupler is preferred, i.e., a coupler capable of a full 360 degree rotation relative to the expanding portion.

It should be understood that the foot wrap may be designed to exclude the support pad 16. However, such is not preferred as the support panel provides additional support and restriction of the bladder movement away from the foot.

It thus is seen that a foot wrap is now provided which maximizes the inflation force of a bladder. While this invention has been described in detail with particular references to the preferred embodiments thereof, it should be understood that many modifications, additions and deletions, in addition to those expressly recited, may be made thereto without departure from the spirit and scope of the invention as set forth in the following claims.

The invention claimed is:

1. A foot wrap comprising,
a support pad;
a fabric binding, said fabric binding having at least a central portion overlying said support pad;
a panel overlying said central portion of said fabric binding, said panel and said central portion of said fabric binding defining a bladder chamber therebetween, and
an expandable bladder that is provided within said bladder chamber such that said expandable bladder is detached from said fabric binding and said panel, wherein said expandable bladder is configured to spin or turn about a center point or axis of rotation of said expandable bladder for rotational movement relative to said bladder chamber of at least 30 degrees, said expandable bladder having an expanding portion and a pneumatic line coupler mounted to said expanding portion and adapted to be coupled to a pneumatic pressure line, said pneumatic line coupler being fully rotatable for 360 degree rotational movement relative to said expanding portion,
wherein said central portion of said fabric binding is non-stretchable and said panel is stretchable, and
wherein said expandable bladder is configured to readily expand in a direction towards a foot of a wearer when inflated with pressurized air by stretching of said panel while expansion of said expandable bladder is restricted in a direction opposite to the foot by said central portion of said fabric binding such that expanding movement of said expandable bladder is deflected or concentrated towards the foot of the wearer and onto a venous plexus vein of the foot.

2. The foot wrap of claim 1 wherein said binding includes a first wing extending from one side of said central portion and a second wing extending from an opposite side of said central portion, and wherein said binding includes a fastener adapted to releasably couple said first wing and said second wing together.

3. A foot wrap comprising,
a support pad;
a non-stretchable, flexible fabric binding coupled to said support pad, said non-stretchable, flexible fabric binding having at least a central portion overlying said support pad;
a stretchable panel overlying said central portion of said non-stretchable, flexible fabric binding, said stretchable panel and said central portion of said non-stretchable, flexible fabric binding defining a bladder chamber, and
an expandable bladder that is provided within said bladder chamber such that said expandable bladder is detached from said non-stretchable, flexible fabric binding and said stretchable panel, wherein said expandable bladder is configured to spin or turn about a center point or axis of rotation of said expandable bladder for rotational movement of said expandable bladder relative to said bladder chamber of at least 30 degrees,
wherein said expandable bladder is configured to readily expand in a direction towards a foot of a wearer when inflated with pressurized air by stretching of said stretchable panel while expansion of said expandable bladder is restricted in a direction opposite to the foot by said central portion of said non-stretchable, flexible fabric binding such that the expanding movement of said expandable bladder is deflected or concentrated towards the foot of the wearer and onto a venous plexus vein of the foot.

4. The foot wrap of claim 1 wherein said expandable bladder is fully rotatable within said bladder chamber for a complete 360 degree rotation therein.

5. The foot wrap of claim 1 wherein said binding includes a first wing extending from one side of said central portion and a second wing extending from an opposite side of said central portion, and wherein said binding includes a fastener adapted to releasably couple said first wing and said second wing together.

6. A foot wrap comprising,
a support pad;
a non-stretchable, flexible fabric binding, said non-stretchable, flexible fabric binding having at least a central portion overlaying said support pad;
a stretchable panel overlying said central portion of said non-stretchable, flexible fabric binding, said stretchable panel and said central portion of said non-stretchable, flexible fabric binding defining a bladder chamber therebetween, and
an expandable bladder that is provided within said bladder chamber such that said expandable bladder is detached from said non-stretchable, flexible fabric binding and said stretchable panel, wherein said expandable bladder is configured to spin or turn about a center point or axis of rotation of said expandable bladder for 360 degree rotation relative to said bladder chamber,
wherein said expandable bladder is configured to readily expand in a direction towards a foot of a wearer when inflated with pressurized air by stretching of said stretchable panel while expansion of said expandable bladder is restricted in a direction opposite to the foot by said central portion of said non-stretchable, flexible fabric binding such that expanding movement of said expandable bladder is deflected or concentrated towards the foot of the wearer and onto a venous plexus vein of the foot.

7. The foot wrap of claim 6 wherein said expandable bladder is rotatable horizontally about a vertical axis.

8. The foot wrap of claim 6 wherein said binding includes a first wing extending from one side of said central portion and a second wing extending from an opposite side of said central portion, and wherein said binding includes a fastener adapted to releasably couple said first wing and said second wing together.

* * * * *